United States Patent
Qian

(10) Patent No.: US 8,551,538 B2
(45) Date of Patent: Oct. 8, 2013

(54) SKIN FORMULATION, PREPARATION AND USES THEREOF

(75) Inventor: Jin Qian, Walnut, CA (US)

(73) Assignee: Golden Pearl Investment LLC, San Marino, CA (US)

( * ) Notice: Subject to any disclaimer, the term of this patent is extended or adjusted under 35 U.S.C. 154(b) by 0 days.

(21) Appl. No.: 13/564,591

(22) Filed: Aug. 1, 2012

(65) Prior Publication Data

US 2013/0045278 A1      Feb. 21, 2013

Related U.S. Application Data

(60) Provisional application No. 61/524,941, filed on Aug. 18, 2011.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2004/0076630 A1 *   4/2004   Pearson et al. ............. 424/146.1

\* cited by examiner

*Primary Examiner* — Michael Meller
(74) *Attorney, Agent, or Firm* — Knobbe, Martens, Olson & Bear LLP

(57) ABSTRACT

Serum compositions for application to skin are described which contain an amniotic fluid extract in combination with embryonic stem cells. Formulations containing the serum composition are also described. The serum compositions and formulations may be applied to skin for treatment of symptoms of aging, wounds, burns, scars or other skin lesions. Methods of preparing the serum compositions and formulations are also disclosed.

2 Claims, 3 Drawing Sheets

Burned

N=4 in each condition
\* p<0.05 (compare with control)

SKIN FORMULATION, PREPARATION AND USES THEREOF

CROSS-REFERENCE TO RELATED APPLICATIONS

This application claims priority to U.S. Provisional Application No. 61/524,941, filed Aug. 18, 2011, which is incorporated herein by reference.

STATEMENT REGARDING FEDERALLY SPONSORED R&D

Not applicable

PARTIES OF JOINT RESEARCH AGREEMENT

Not applicable

REFERENCE TO SEQUENCE LISTING, TABLE, OR COMPUTER PROGRAM LISTING

Not applicable

BACKGROUND OF THE INVENTION

1. Field of the Invention

The invention relates generally to compositions containing embryonic stem cells and extracellular fluid which may be applied to the skin to obtain beneficial results including a decrease in the appearance of aging of the skin, and treatment for healing wounds, burns and scars.

2. Description of the Related Art

Skin is the largest organ of the human body. Not only does this 1.8 square meter network of nerves, blood vessels, pigments, and fibrous cells as well as sweat and oil glands play a key role in protecting the body against pathogens, but skin also prevents excessive water loss. Skin also has other important functions such as insulation, temperature homeostasis, sensation, synthesis of vitamin D, and the protection of vitamin B. Skin care, especially anti-aging care products, focus on one or more of the following aspects: antioxidant protection, moisture retention, and/or promoting skin cell growth.

Many synthetic chemicals as well as natural extracts have been identified as effective ingredients for skin care. However, there are also misunderstandings about the function of these ingredients. Many "anti-aging" products are, in fact, make-up products using compounds such as silicon to cover up lines and wrinkles. Natural ingredients are generally gentler to skin than synthetic chemicals with fewer unwelcome effects.

The present inventors have addressed the problem of providing an effective formulation for the skin in which the active ingredients are derived from natural products.

Further aspects, features and advantages of this invention will become apparent from the detailed description of the preferred embodiments which follow.

SUMMARY OF THE INVENTION

Embodiments of the invention are directed to methods of preparing a serum composition for application to skin which include one or more of the following steps:
(1) incubating eggs to form an embryoblast including an embryo and amniotic fluid,
(2) extracting amniotic fluid from the eggs,
(3) extracting the embryo or a portion of the embryo,
(4) homogenizing the embryo,
(5) centrifuging the embryo to obtain an embryo supernatant and an embryo pellet, and
(6) mixing the amniotic fluid from step (2) with the embryo supernatant and optionally the embryo pellet from step (5) at a ratio of 70-100% amniotic fluid and 0-30% embryo supernatant to provide the serum composition.

In preferred embodiments, the egg is a chicken egg and the incubation period is 5-14 days, more preferably the incubation period is 7-8 days. The serum composition may be used directly or combined with other components. In some preferred embodiments, proteins, peptides, lipids, vitamins, minerals, moisturizers, plant extracts and/or preservatives are added to the serum composition.

Embodiments of the invention are directed to a serum composition which includes amniotic fluid and homogenized embryo mixed at a ratio of 70-100% amniotic fluid with 0-30% homogenized embryo, obtained from a chicken egg incubated for a period of 5-14 days after fertilization, preferably, the incubation period is 7-8 days.

Preferred embodiments of the invention are directed to formulations that contain the serum composition described above in combination with one or more of the following: polyethylene glycol (PEG), hyaluronic acid, glycerin, soy protein, silk protein, ginko biloba, green tea extract, grape seed oil, rye seed extract, argireline, gluconodeltaoactone and sodium benzoate.

In preferred embodiments, serum compositions and formulations containing the serum composition according to the invention are used in a method of improving the appearance of skin by applying the serum composition or formulation in an effective amount to an individual in need thereof. In preferred embodiments, the formulation is applied to the face, neck and/or hands. Preferably, the formulation is applied 1-3 times per day.

In preferred embodiments, compositions and formulations containing the serum composition according to the invention are used in a method of treating burns by applying the serum composition or a formulation containing the serum composition in an effective amount to an individual in need thereof.

In preferred embodiments, serum compositions and formulations containing the serum composition according to the invention are used in a method of treating a scar or skin lesion by applying the serum composition or a formulation containing the serum composition in an effective amount to an individual in need thereof In preferred embodiments, serum compositions and formulations containing the serum composition according to the invention are used in a method of treating wounds by applying the serum composition or a formulation containing the serum composition in an effective amount to an individual in need thereof. In some embodiments, the wound is a diabetic wound.

In preferred embodiments, the serum composition or formulation containing the serum composition is applied 1-3 times per day.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
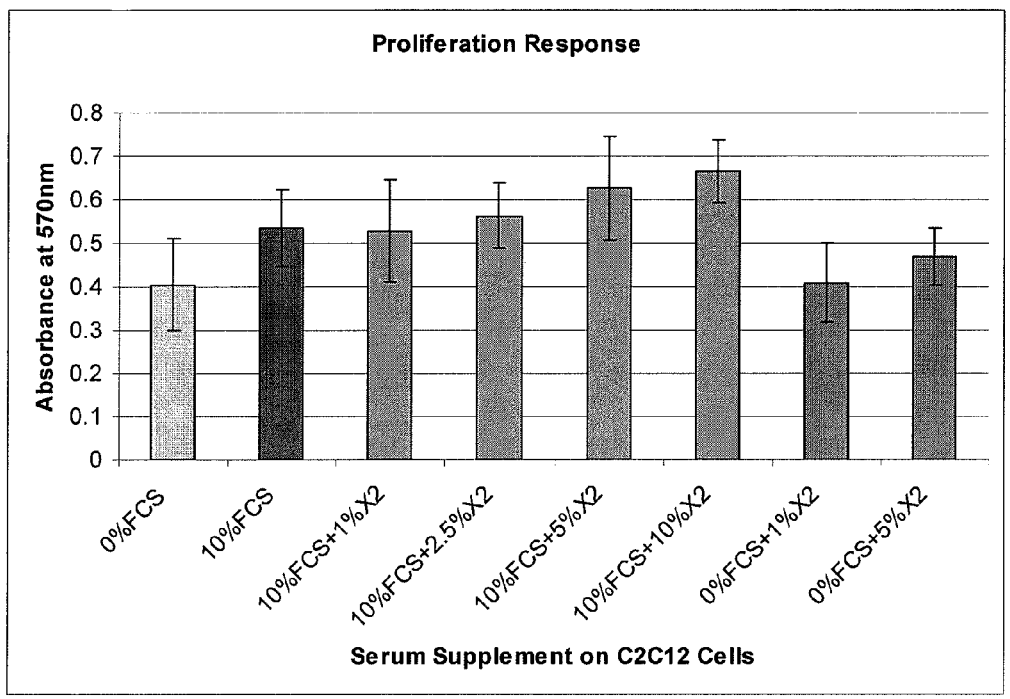
FIG. 1 shows $C_2C_{12}$ cells seeded at a density of 5000 cells per well in a 96 well plate and cultured for 48 hours with DMEM medium under the indicated condition (n=12). The assay was performed as described by INVITROGEN's MTT Cell Proliferation Kit protocol. Extract X2 was added at a concentration of 0-10% in the presence of fetal calf serum (FCS).

While the described embodiment represents the preferred embodiment of the present invention, it is to be understood that modifications will occur to those skilled in the art without departing from the spirit of the invention. The scope of the invention is therefore to be determined solely by the appended claims.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

Embodiments of the invention are directed toward treating patients with skin diseases, undesirable skin conditions or appearances and toward treating older skin to provide a younger appearance, i.e., preventing, inhibiting or relieving the effects of aging on skin and thereby improving the appearance of wrinkled, lined, dry, flaky, aged or photo damaged skin and improving skin thickness, elasticity, flexibility and/or plumpness at one or more particular sites. Preferred embodiments of the invention are directed to treatment of wounds including diabetic wounds, scars, skin lesions and burns. More specifically, "treatment" is intended to mean providing a therapeutically detectable and beneficial effect on a patient suffering from a skin condition or appearance which the patient has found to be undesirable.

The term "effective amount" is used to indicate an amount of an active compound that elicits the biological or medicinal response indicated. This response may occur in a tissue, system, animal or human and includes alleviation of the symptoms of the condition or disease being treated.

Embodiments of the present invention are directed to serum compositions and formulations containing the serum compositions for treatment of symptoms associated with aging of the skin, treatment of dermatological diseases, scars, burns, wounds, diabetic wounds and injuries related to the skin. The present inventors have discovered natural active compounds that support health of skin cells. These gentle and effective compounds are extracted from Epiblast-derived Stem Cells that are rich in natural growth factors, amino acids, polypeptides, multi-vitamins, and minerals which could stimulate skin cell regeneration. The present inventors combined these Epiblast-derived Stem Cell extracts with natural Extra-Cellular Fluid (ECF), thereby creating a gentle but advanced Anti-Aging factor, "Extract X2".

During embryogenesis, a fertilized egg divides (cleavage), forms a ball of cells (morula), develops a cavity (blastocyst stage), and forms the three primary germ layers of cells that will ultimately give rise to all the cell types of the body (gastrula stage), and ultimately generates all the specialized tissues and organs of a mature organism. The epiblast is a tissue type derived either from the inner cell mass in mammals or the blastodisc in birds and reptiles that becomes the embryo. The growth rate of cell mass during early embryogenesis is the fastest growth period in the whole life of any animal, showing linear growth. In order to support such a rapid growth, early embryonic cells must produce a high level of growth promoting elements, and at the same time sufficient nutritional factors must be present in the environment. Embodiments of the invention are directed to extraction of these growth and nutritional elements for preparation of a formulation for application to skin. Without intending to be limited by theory, it is thought that the serum according to embodiments of the invention is able to fool the skin cells to act like younger cells in growth phase. As most, if not all, growth factors were initially discovered in studying embryogenesis, the growth factors in extracts described herein are generally present at biologic levels. Even though the level of any given growth factor may be low compared to a chemically synthesized formulation, the combination of factors found in serum composition and formulations containing the serum compositions according to embodiments of the invention could act synergistically. In addition, other regulatory elements, such as peptides and cytokines, are also present.

An incomplete list of growth factors involved in embryogenesis is the following: Adrenomedullin (AM); Anterior chamber growth factor; Autocrine growth factor; Basic fibroblast growth factor (FGF2); Bone morphogenetic protein (BMP); Bone morphogenetic protein 2 (BMP2); Bone morphogenetic protein 3 (BMP3); Bone morphogenetic protein 4 (BMP4); Bone morphogenetic protein 7 (BMP7); Bone morphogenetic protein 8B (BMP8B); Brain-derived neurotrophic factor (BDNF); Connective tissue growth factor (CTGF); Epidermal growth factor (EGF); Erythropoietin (EPO); Fibroblast growth factor (FGF); Fibroblast growth factor 1 (FGF1); Fibroblast growth factor 3 (FGF3); Fibroblast growth factor 4 (FGF4); Fibroblast growth factor 5 (FGF5); Fibroblast growth factor 7 (FGF7); Fibroblast growth factor 8 (FGF8); Glial growth factor (GGF); Granulocyte colon-stimulating factor (G-CSF); Granulocyte macrophage colon-stimulating factor (GM-CSF); Growth differentiation factor-9 (GDF9); Hepatocyte growth factor (HGF); Hepatoma-derived growth factor (HDGF); Insulin-like growth factor (IGF-I); Insulin-like growth factor II (IGF-II); Interleukin 3 (IL-3); Interleukin 6 (IL-6); Keratinocyte growth factor (KGF); Migration-stimulating factor; Myostatin (GDF-8); Nerve growth factor (NGF); Placental growth factor (PlGF); Platelet-derived growth factor (PDGF); Thrombopoietin (TPO); Transforming growth factor-α (TGF-α); Transforming growth factor-β (TGF-β); Transforming growth factor-β1 (TGF-β1); Transforming growth factor-β2 (TGF-β2); Transforming growth factor-β3 (TGF-β3); vascular endothelial growth factors (VEGF); and Wnt protein family.

The following minerals are involved in embryogenesis: Sodium, Potassium, Chloride, Calcium, Phosphate, Magnesium, and trace metals (Iron, Copper, Zinc, Manganese, Selenium, and Molybdenum), etc.

The following vitamins are involved in embryogenesis: Vitamin A, Vitamin B6, Folic acid, Vitamin B9, Vitamin B12, Vitamin C, Vitamin D3, and Vitamin E, etc.

The following additional biochemical components are involved in embryogenesis: Glucose, Cholesterol, Triglyceride, Urea, Albumin, Globulin, Bicarbonate, Oligo-peptides, CoQ10, Carnitine, Alpha-fetoprotein, Superoxide Dismutase, DNA, and RNA, etc.

Serum compositions according to the invention are termed "Extract X2". As the Extract X2 composition according to embodiments of the invention is obtained from embryonic cells at an early time of development, most if not all of the above components are present in the Extract X2 composition and formulations containing the Extract X2 composition.

Formulations containing an Extract X2 composition can be used to treat symptoms of skin aging including but not limited to improvement in skin firmness, whitening, moisturizing, dark spot reducing, wrinkle reducing, gloss, and elasticity. Formulations according to embodiments of the invention are also useful to treat a variety of skin conditions including but not limited to scars, burns, and wounds including diabetic wounds.

In some preferred embodiments, a blend of hyaluronic acid, soy proteins and/or silk proteins helps strengthen and tighten the junction between cells to lock in moisture, strengthening the lipid barrier and preventing transepidermal water loss. In some preferred embodiments, antioxidants, such as green tea, ginkgo biloba extracts and/or grape seed oil establish a powerful anti-radical defense system, shield against pollution and skin stressors. In some preferred embodiments, rye seed extract and/or oligo-peptide are added. The Extract X2 serum soothes facial wrinkles, tightens skin and reveals moist delicate skin. Compositions according to embodiments of the invention reduce the appearance of fine lines and wrinkles, brighten skin tone, and leave skin feeling soft, smooth, elastic, and firm.

Preparation of the Formulation

The starting material is the inner cell mass or epiblast (blastodisc in mammals and birds) derived from the fertilized eggs of birds, reptiles, amphibians or fish including but not limited to chickens, ostrich, turkeys, geese, ducks, and turtles. The cells of the inner cell mass are the cells from which the embryo will develop. In a most preferred embodiment, the inner cell mass from fertilized chicken eggs is used as the starting material. The eggs are incubated 5-14 days, preferable 7-8 days after fertilization. After the incubation period, the eggs are opened and the amniotic fluid is extracted by any means known in the art. Typically, the amniotic fluid is simply extracted by means of a syringe from the amniotic cavity. The extracted amniotic fluid is centrifuged to remove cells and debris and can be used immediately or stored at −20° C., preferably at −80° C.

The embryo portion from the epiblast is washed, preferably with deionized water or buffered solution such as phosphate buffered saline. The embryos are homogenized and centrifuged to separate larger particles. The supernatant is removed and may be used immediately or stored at −20° C., preferably at −80° C. The pellet, which is useful in heavier formulations such as creams, can be used immediately or lyophilized for future use.

In preferred embodiments, the final composition contains 50-100% amniotic fluid and 0-50% extracted embryos. So the formulation may have a ratio from 1:1 to 100:0 amniotic fluid: extracted embryos. In some embodiments, the composition may contain substantially only amniotic fluid. Preferably the final composition contains 70-100% of amniotic fluid and 0-30% of embryos. In preferred embodiments, the range is 70:30 to 100:0 amniotic fluid: extracted embryos. In preferred embodiments, ratios of 100:0, 95:5, 90:10, 85:15, 80:20, 75:25, and 70:30 amniotic fluid:extracted embryos may be used.

In preferred embodiments, polyethylene glycol 150 Distearate (PEG 150 Distearate) is added to protect large molecules and improve the feel of the formulation on skin. PEG is added at a concentration of 0.5-5% (w/v), preferably 0.5-2% (w/v), most preferably around 1% (w/v). In preferred embodiments, any PEG of molecular weight range 4,000-15,000 may be used. In some embodiments, large molecular weight proteins, such as bovine serum albumin or soy protein, may be added to the composition. In some embodiments, glyceryl monostearate may be substituted for PEG or used in addition to PEG.

In preferred embodiments, moisturizers may be added to the final formulation. Preferably hyaluronic acid is added at a concentration of 0.1-5% (w/v), preferably, 0.2-2% (w/v), most preferably about 0.5% (w/v). In some embodiments, glycerin, preferably vegetable-derived, is added at a concentration of 2-10% (v/v), preferably, 5-7% (v/v), most preferably about 6% (v/v). Proteins, preferably hydrolyzed proteins, may be added including but not limited to soy protein and silk protein. These proteins are added in a preferred concentration range of 0.5-5%, preferably 1-2%.

In preferred embodiments, the formulation may include antioxidant plant extracts such as Ginko Biloba at a concentration of 1-5% (v/v), preferably 2-4% (v/v), more preferably about 3% (v/v). Preferably, the formulation may contain green tea extract at a concentration of 1-5% (v/v), preferably 1-3% (v/v), more preferably about 2% (v/v). Preferably, the formulation may contain grape seed oil at a concentration of 1-5% (v/v), preferably 1-3% (v/v), more preferably about 2% (v/v). In some embodiments, the formulation may include one or more selected from extracts from citrus, olive tree, rosemary, sage, thyme, chamomile, berries, fruits, vegetables, herbs, cereals, tree materials, plant sprouts, and seeds. In some embodiments, the formulation may include one or more selected from vitamin A, thiamine, niacinamide, pyridoxine, riboflavin, cyanocobalamin, biotin, pantothenic acid, vitamin C, vitamin D, vitamin E, vitamin K and folic acid.

In preferred embodiments, the formulation may contain compounds which reduce the degree or appearance of existing wrinkles such as rye seed extract at a concentration of 1-5% (v/v), preferably 2-4% (v/v), more preferably about 3% (v/v) and/or extra oligo-peptides such as argireline at a preferred concentration of 0.5-2% (v/v), preferably about 1% (v/v). In some embodiments, a formulation according to the invention may contain one or more selected from extracts from cacao beans, cola nuts, and caffeine, theobromine, and theophylline, coffee berry, aloe, green tea, centella asiatica, Coenzyme Q10, and the like.

In preferred embodiments, the composition contains a preservative. Preferably, the preservative is one that is accepted by EOCERT as an acceptable preservative in certified organic cosmetics such as gluconodeltalactone and/or sodium benzoate. Preferably, the concentration is 1-3% (w/v), more preferably about 1.5% (w/v) in total. Alternative preservatives which may be used include parabens (methyl-, ethyl-, propyl- and butyl-), urea derivatives such as imidazolidinyl urea and diazolidinyl urea, isothiazolones (methylchloro-, methylisothiazolinone), halogen organic actives (iodopropynyl butylcarbamate, methyl-dibromo glutaronitrile), organic acids, chloracetamine, EDTA, phenoxyethanol, triclosan, DMDM-hydantoin and quaternium-15. In some preferred embodiments, the preservative is selected from natural preservatives such as extracts of willow bark, radish root ferment filtrate, grapefruit seed, extracts of rosemary, essential oils such as tea tree, neem seed and thyme and vitamins E or C.

In preferred embodiments, the components of the formulation are approved for use in certified organic cosmetics.

Embodiments of the skin formulation can contain optional ingredients used commonly in external preparations for the skin. Preferred examples of such optional ingredients include: oils/waxes such as macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, glyceryl di-2-heptylundecanoate, glyceryl tri-2-ethylhexanoate, trimethylolpropane tri-2-ethylhexanoate, trimethylolpropane triisostearate, and pentaerythritol tetra-2-ethylhexonate; silicone oil, such as chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexanesiloxane; modified polysiloxanes such as amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium laurylsulfate, and triethanolamine alkylsulfate ether; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium hydroxide-1-carboxyethyloxy disodium salt), betaine-based surfactants (such as alkyl betaine, amide betaine, and sulfo betaine), and acylmethyl taurine; nonionic surfactants such as sorbitan fatty acid esters (such as sorbitan monostearate and sorbitan sesquioleate), glycerin fatty acid esters (such as glycerin monostearate), propyleneglycol fatty acid esters (such as propyleneglycol monostearate), cured castor oil derivatives, glycerol alkyl ether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glyceryl monoisostearate), POE fatty acid esters (such as polyethyleneglycol monooleate and POE distearate), POE alkyl ethers (such as POE2-octyldodecyl ether), POE alkylphenyl ethers (such as POE nonylphenyl ether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glycoside; polyvalent alcohols such as polyethylene glycol, glycerin, 1,3-butylene glycol, erythritol, sorbitol, xylitol, maltitol, propylene glycol, dipropylene glycoi, diglycerin, isoprene glycol, 1,2-pentanediol, 2,4-hexanediol, 1,2-hexanediol, and 1,2-octanediol; moisture components such as sodium pyrrolidone carboxylate, lactate, and sodium lactate; fine particles such as mica, talc, kaolin, synthetic mica, calcium carbonate, magnesium carbonate, silicic anhydride (silica), aluminum oxide, and barium sulfate, whose surfaces may be treated; inorganic pigments such as red iron oxide, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204; organic fine particles such as polyethylene powder, polymethyl methacrylate, nylon powder, and organopolysiloxane elastomer; p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl)benzotriazole, and 4-methoxy-4'-t-butyldibenzoylmethane; lower alcohols such as ethanol and isopropanol; vitamins such as vitamin A or derivatives thereof; vitamin B types such as vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof; vitamin E types such as α-tocopherol, β-tocopherol, γ-tocopherol, and vitamin E acetate, vitamin D types, vitamin H, pantothenic acid, pantethine, and pyrroloquinoline quinone; and antibacterial agents such as phenoxyethanol.

Embodiments of the invention directed to external application for promoting wound healing may preferably contain ingredients effective to the regeneration of the wounded dermal tissue, including but not limited to an antibiotic substance for preventing microbial infection such as penicillin, fradiomycin, tetracycline, or a salt thereof, a sterilizer such as acrinol or isodine, or the like. In more preferred embodiments natural extracts are used such as Aspen Bark Extract, Leuconostoc/Radish Root Ferment Filtrate, Lavender Extract, Lemon Peel Extract, Thyme Extract, Goldenseal Extract, Echinacea Extract, and Hypericum Extract.

Embodiments of the invention directed to external application for promoting healing of burns may preferably contain additional ingredients effective to treat, heal or relieve pain from burn injuries such as antimicrobials including but not limited to bacitracin, silver sulfadiazine, mafenide, silver nitrate, and povidone-iodine, antibiotics including but not limited to oxacillin, mezlocillin and gentamicin, a sterilizer such as acrinol or isodine, and topical pain medications.

Embodiments of the skin formulation may be in any form suitable for retaining the formulation on the skin for a sufficient period of time, such as a serum, lotion, emulsion, ointment, or cream. In some embodiments, the skin formulation may be used in a cosmetic composition.

Administration may be to any part of the body. However, in preferred embodiments directed to anti-aging formulations, administration is preferably to exposed skin such as face, neck and hands. The formulation may be administered to all or part of a given area such as the face. In preferred embodiments directed to a particular dermatological disorder or injury such as a wound or burn, administration is to the affected area.

Administration may be 1 or more times daily until sufficient relief from symptoms is obtained. Preferably, administration is from 1-5 times daily, more preferably, 1-2 times daily. In some embodiments, once daily administration is sufficient. Administration may be continual for a period of time until symptoms are relieved or eliminated or intermittent if the patient suffers from recurring symptoms.

EXAMPLES

Example 1

Method of Preparation of Serum Extract X2

Fertilized chicken eggs were incubated in an avian egg incubator at 100° C. for 8 days with automatic turning. The incubated eggs were opened and amniotic fluid is extracted by a needle. The amniotic fluid was centrifuged at 4,000 rpm for 10 minutes. The supernatant was removed.

Embryos were washed with deionized $H_2O$ or phosphate buffered saline (PBS). The embryos or a portion of the embryos were homogenized and then centrifuged at 6,000 rpm for 15 minutes. The supernatant was removed. The pellet was dried by lyophilization for future use.

The extracted amniotic fluid and embryos were mixed at ratio from 70% to 100% of amniotic fluid with 30% to 0% of extracted embryos, depending on the final product.

Example 2

Effect of Serum Extract X2 on Cell Growth

FIG. 1 shows $C_2C_{12}$ cells seeded at densities of 5000 cells per well in a 96 well plate and cultured for 48 hours with DMEM medium under the indicated condition (n=12). The assay was performed according to INVITROGEN's MTT Cell Proliferation Kit protocol. Serum Extract X2 at a ratio of amniotic fluid:extracted embryos of 100:0 were added at a concentration of 0-10% in the presence of fetal calf serum (FCS). The results suggest that serum Extract X2 has sufficient nutritional supplements to replace FCS in cell culture (light blue bars in the figure). More important, serum Extract X2 synergistically promoted cell proliferation with FCS (10% FCS vs. 10% FCS+10% X2, P<0.05).

Example 3

Method of Preparation of Formulation Containing Extract X2

1% (w/v) PEG, hyaluronic acid at 0.5% (w/v), vegetable glycerin at 6% (v/v), soy proteins at 2% (v/v), silk proteins at 1% (v/v), Ginkgo Biloba at 3% (v/v), Green Tea extract at 2% (v/v), Grape Seed Oil at 2% (v/v), Rye Seed Extract at 3% (v/v), and extra oligo-peptide, such as Argireline at 1% (v/v) was added into the final formulation which had 10% Extract X2.

Gluconodeltalactone and Sodium Benzoate, (both are accepted by ECOCERT as a preservatives for use in certified organic cosmetics), were added at 1.5% (w/v) total into the final formulation.

TABLE 1

Exemplary formulation containing Extract X2

| Component | Concentration |
|---|---|
| Extract X2 | 10% (v/v) |
| PEG 150 Distearate | 1% (w/v) |
| hyaluronic Acid | 0.5% (w/v) |
| DL-Pathenol | 1.0% (w/v) |
| vegetable glycerin | 6% (v/v) |
| Quaternium-79 Hydrolyzed Soy Protein | 2% (v/v) |
| Hydrolyzed Silk Protein | 1% (v/v) |
| *Ginkgo Biloba* Leaf Extract | 3% (v/v) |
| *Camellia Sinensis* Leaf (Green Tea) Extract | 2% (v/v) |
| *Vitis Vinifera* (Grape) Seed Oil | 2% (v/v) |
| *Secale Cereale* (Rye) Seed Extract | 3% (v/v) |
| Acetyl Hexapeptide-8 (Argireline) | 1% (v/v) |
| Gluconodeltalactone and Sodium Benzoate | 1.5% (w/v) |
| water | 67% (v/v) |

Example 4

Effect of Extract X2 Formulation on Skin

Figure 2:
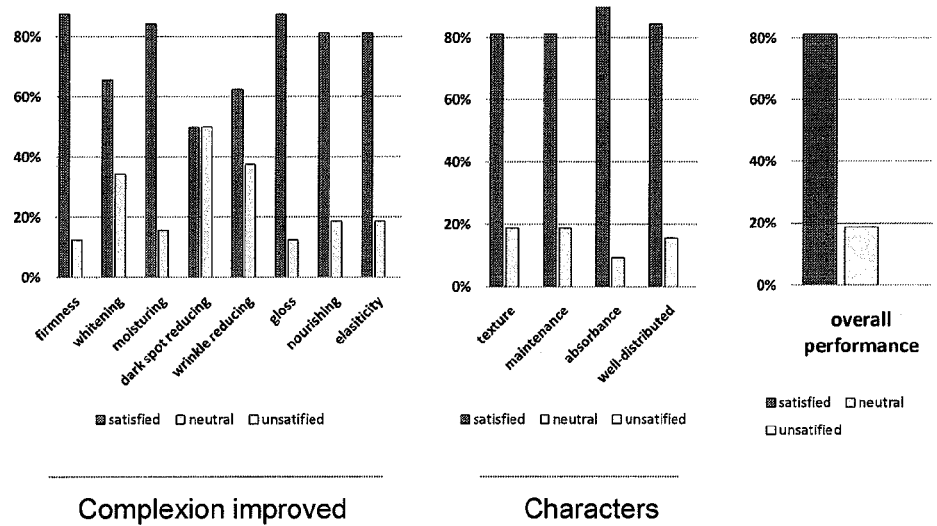
FIG. 2 shows the results of a study using a formulation containing Extract X2. A total of 32 females from age 35 to 60 years old participated in this study. Dark bars indicate satisfied responses. Lighter bars indicate neutral responses. There were no unsatisfied responses in any of the tested categories.

A formulation as in Table 1 above was tested in 32 females aged 35-60 years old for 30 days. A number of criteria were evaluated including skin firmness, whitening, moisturizing, dark spot reducing, wrinkle reducing, gloss, nourishing, and elasticity. Texture, maintenance (stability), absorbance and distribution of the product on skin were also evaluated. The results are shown in FIG. 2. In all categories, the results were positive. For overall performance, 80% were satisfied with the formulation. No side effects were reported in this study. No individuals were unsatisfied with the results after 30 days of testing.

Example 5

Effect of Extract X2 Formulation on Burn Injury

Figure 3:
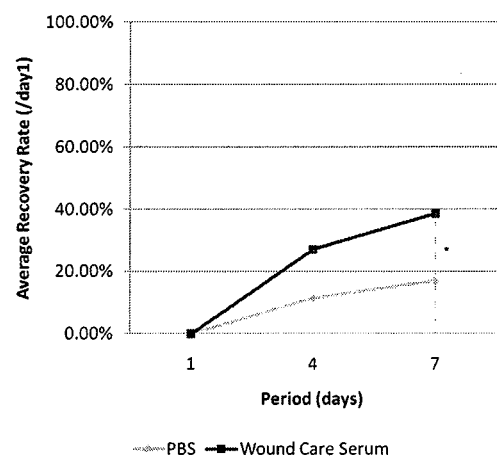
FIG. 3 shows C57BL mice which were introduced with controlled burn injury and treated twice a day with specially formulated serum containing Extract X2. A significant speedy recovery was observed in days 1-7 ($p<0.05$) compared to control (PBS). For each condition, n=4; $p<0.05$ (compared to control).

Anesthetized male C57BL mice were introduced with controlled burn injury and treated twice a day with specially formulated serum as described in Table 2 below containing Extract X2. A significant speedy recovery was observed in days 1-7 (p<0.05) compared to control (PBS) (FIG. 3).

TABLE 2

Exemplary formulation for burn injury containing Extract X2

| Component | Concentration |
|---|---|
| Extract X2 | 10% (v/v) |
| *Aloe Vera* 200x | 0.4% (w/v) |
| hyaluronic Acid | 1.0% (w/v) |
| DL-Pathenol | 1.0% (w/v) |
| vegetable glycerin | 6% (v/v) |
| Quaternium-79 Hydrolyzed Soy Protein | 2% (v/v) |
| Organicals Acne Extract | 4% (v/v) |
| Organicals Tissue Repair | 4% (v/v) |
| Niacinamide | 2% (v/v) |
| Vitamin C | 2% (v/v) |
| Willow Bark Extract | 2.5% (v/v) |
| *Camellia Sinensis* Leaf (Green Tea) Extract | 2% (v/v) |
| Yeast Extract | 2% (v/v) |
| *Vitis Vinifera* (Grape) Seed Oil | 2% (v/v) |
| Hydrocotyl (*Centella Asiatica*) Extract | 3% (v/v) |
| *Glycrrhiza Glabra* (Licorice) Root Extract | 2% (v/v) |
| *Olea Europaea* (Olive) Leaf Extract | 2.0% (v/v) |
| *Leuconostoc*/Radish Root Ferment Filtrate | 2.0% (w/v) |
| water | 50.1% (v/v) |

Example 6

Effect of Extract X2 Formulation on Wounds

A formulation as in Example 3 above is prepared except that Extract X2 is prepared at a ratio of amniotic fluid:extracted embryos of 90:10 and the formulation further contains at least one of Aspen Bark Extract, Lavender Extract, Lemon Peel Extract, Thyme Extract, Goldenseal Extract, Echinacea Extract, or Hypericum Extract. The formulation is applied 2 times a day to a skin wound.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of making a serum composition for application to the skin of a human in need thereof consisting essentially of:
   a) incubating chicken eggs to form an embryoblast containing an embryo and amniotic fluid for 5-14 days;
   b) extracting amniotic fluid from the eggs;
   c) extracting the embryo from the eggs;
   d) homogenizing the embryo or a portion thereof;
   e) centrifuging the embryo to obtain an embryo supernatant and an embryo pellet;
   f) mixing the amniotic fluid from step (b) with the embryo supernatant and the embryo pellet from step (e) at a ratio of 70-100% amniotic fluid and 0-30% embryo supernatant to provide an amniotic fluid/embryo supernatant/pellet;
   g) adding at least one component selected from the group consisting of polyethylene glycol, hyaluronic acid, glycerin, soy protein, silk protein, ginko biloba, green tea extract, grape seed oil, rye seed extract, argireline, gluconodeltalactone, and sodium benzoate to said amniotic fluid/embryo supernatant/pellet to form said serum composition;
   h) applying the serum composition to the skin of the human in need thereof.

2. The method of claim 1, wherein the incubation period in step (a) is 7-8 days.

\* \* \* \* \*